United States Patent
Nishida et al.

(10) Patent No.: US 7,646,489 B2
(45) Date of Patent: Jan. 12, 2010

(54) APPARATUS AND METHOD FOR MEASURING FILM THICKNESS

(75) Inventors: Kazufumi Nishida, Musashino (JP); Shigeyuki Kakuta, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 73 days.

(21) Appl. No.: 12/108,235

(22) Filed: Apr. 23, 2008

(65) Prior Publication Data
US 2008/0266550 A1 Oct. 30, 2008

(30) Foreign Application Priority Data
Apr. 25, 2007 (JP) .............................. 2007-115488

(51) Int. Cl.
- G01B 9/02 (2006.01)
- G01J 3/45 (2006.01)
- G01B 11/02 (2006.01)
- G01B 11/28 (2006.01)

(52) U.S. Cl. .................. 356/504; 356/630; 356/497; 356/451

(58) Field of Classification Search .................. 356/451, 356/479, 497, 481, 517, 503, 504, 630, 632
See application file for complete search history.

(56) References Cited

U.S. PATENT DOCUMENTS

| | | | | |
|---|---|---|---|---|
| 4,885,709 A | * | 12/1989 | Edgar et al. ................... | 702/30 |
| 7,408,649 B2 | * | 8/2008 | Freischlad et al. .......... | 356/497 |
| 7,428,056 B2 | * | 9/2008 | Freischlad et al. .......... | 356/497 |
| 2007/0091317 A1 | * | 4/2007 | Freischlad et al. .......... | 356/511 |
| 2007/0091318 A1 | * | 4/2007 | Freishlad et al. ............ | 356/511 |

FOREIGN PATENT DOCUMENTS

| | | |
|---|---|---|
| JP | 11-314298 A | 11/1999 |
| JP | 2005-308394 A | 4/2005 |

\* cited by examiner

*Primary Examiner*—Patrick J Connolly
(74) *Attorney, Agent, or Firm*—Sughrue Mion, PLLC

(57) ABSTRACT

A film thickness measuring apparatus of the present invention includes: a light source that emits white light to be irradiated onto a multilayer thin film; a spectroscope that disperses reflected light obtained as a result of irradiating the white light onto the multilayer thin film in order to obtain reflectance spectrums; and a computation section, said computation section including: a setting section that sets a plurality of wavelength ranges for the reflectance spectrums; a first conversion section that obtains wavenumber range reflectance spectrums by re-sequencing, among the reflectance spectrums, reflectance spectrums in the plurality of wavelength ranges set in said setting section at equal intervals, respectively; a second conversion section that converts the wavenumber range reflectance spectrums in the plurality of wavelength ranges obtained in said first conversion section into power spectrums, respectively; and a calculation section that obtains a film thickness of the multilayer thin film based on the power spectrums.

9 Claims, 6 Drawing Sheets

APPARATUS AND METHOD FOR MEASURING FILM THICKNESS

BACKGROUND OF THE INVENTION

1. Field of the Invention

The present invention relates to a film thickness measuring apparatus and method for measuring the film thickness of a multilayer thin film.

Priority is claimed on Japanese Patent Application No. 2007-115488, filed on Apr. 25, 2007, the content of which is incorporated herein by reference.

2. Description of Related Art

A film thickness measuring apparatus is used for measuring the film thickness distribution and the film thickness error of a multilayer thin film including a flexible substrate, a multilayer composite film sheet, and other kinds of multilayer thin films. FIG. 5 is a diagram showing a schematic configuration of a conventional film thickness measuring apparatus. As shown in FIG. 5, a conventional film thickness measuring apparatus 100 is provided with a white light source device 101, an irradiation fiber 102, a light receiving fiber 103, a spectroscope 104, and a computation section 105. The film thickness measuring apparatus 100 measures the film thickness of a film 200 formed with a plurality of layers 201 to 203.

The white light source device 101 is a light source that emits white light. The irradiation fiber 102 is a light guiding member that guides the light emitted from the white light source device 101 to the film 200 so as to irradiate the light onto the film 200. The light receiving fiber 103 is a light guiding member that guides reflected light from the film 200 to the spectroscope 104.

The spectroscope 104 disperses the reflected light from the film 200 that has been guided by the light receiving fiber 103, and further converts it into electrical signals to obtain reflectance spectrums.

The computation section 105 performs a predetermined computation for the reflectance spectrums obtained in the spectroscope 104 to measure the film thickness of the film 200. Specifically, the computation section 105 performs a computation to select one predetermined wavelength range among the reflectance spectrums obtained in the spectroscope 104, and a computation to obtain wavenumber range reflectance spectrums by re-sequencing the reflectance spectrums within the selected wavelength range at equal intervals. Next, the computation section 105 performs a computation to obtain a power spectrum by performing a Fourier conversion on the signals that indicate the wavenumber range reflectance spectrums. Next, the computation section 105 performs a computation to detect peaks in the power spectrum.

In the above configuration, the white light emitted from the white light source device 101 is guided by the irradiation fiber 102 so as to be irradiated from the layer 201 side onto the film 200. Among the reflected light obtained as a result of irradiating the white light onto the film 200, the reflected light that has been incident on the light receiving fiber 103 is guided to the spectroscope 104 by the light receiving fiber 103. This reflected light is dispersed in the spectroscope 104, and furthermore it is photoelectrically converted. The electrical signal obtained as a result of the photoelectric conversion is inputted to the computation section 105, and is subjected to the various computations mentioned above. As a result of these computations, the film thickness of the film 200 is found.

The white light reflected on each interfacial surface of the respective layers 201 to 203 that form the film 200 has an optical path difference according to the distance between the respective interfacial surfaces (film thickness). Since the white light having optical path differences mutually interferes with each other, a cyclical interference pattern emerges in a wavenumber range reflectance spectrum. A power spectrum that is obtained as a result of performing a Fourier conversion on this cyclical interference pattern has a peak at a frequency according to the optical path difference. Therefore, by detecting this peak, an optical path length difference (optical film thickness) can be found.

FIG. 6 shows an example of a power spectrum obtained by the film thickness measuring device 100. The film thickness measurement result shown in FIG. 6 is a result of measuring the film 200 formed with the layer 201, the layer 202, and the layer 203. The refraction factor of the film 201 is 1.6 and the film thickness of the layer 201 is 5 μm. The refraction factor of the film 202 is 1.7 and the film thickness of the layer 202 is 12 μm. The refraction factor of the film 203 is 1.6 and the film thickness of the layer 203 is 3 μm. The optical film thicknesses of the layers 201 to 203 are found as a product of the film thickness and the refraction factor, and they are 8.0 μm, 20.4 μm, and 4.8 μm. Moreover, in the graph shown in FIG. 6, the horizontal axis represents the optical film thickness, and the vertical axis represents the intensity (arbitrary units).

Referring to FIG. 6, it can be seen that there is a plurality of peaks emerging. The horizontal positions of these peaks indicate the optical distance between the respective interfacial surfaces, and the heights of the peaks indicate products of amplitude reflectances on the two interfacial surfaces. Specifically, in FIG. 6, there are six peaks emerging. The first peak P101 emerges at 4.8 μm indicating the optical film thickness of the layer 203. The second peak P102 emerges at 8.0 μm indicating the optical film thickness of the layer 201. The third peak P103 emerges at 20.4 μm indicating the optical film thickness of the layer 202.

The fourth peak P104 emerges at 25.2 μm indicating the sum of the optical film thickness of the layer 202 and the optical film thickness of the layer 203. The fifth peak P105 emerges at 28.4 μm indicating the sum of the optical film thickness of the layer 201 and the optical film thickness of the layer 202. The sixth peak P106 emerges at 33.2 μm indicating the sum of the optical film thicknesses of the layers 201 to 203 (that is, the optical film thickness of the film 200). Thereby, based on the position of the peak of the power spectrum, the optical film thicknesses of the respective layers 201 to 203 forming the film 200 and the optical film thickness of the film 200 can be found.

For the detail of the conventional apparatus and method for measuring film thickness, refer for example to Japanese Unexamined Patent Application, First Publication No. 2005-308394, and Japanese Unexamined Patent Application, First Publication No. Hei 11-314298.

The positions of the peaks of the power spectrum obtained in the above mentioned conventional apparatus and method for measuring film thickness indicate the optical distances between the respective interfacial surfaces. Therefore, there is a problem that the position of the interfacial surface on which the peak has been obtained with respect to the top most surface (the interfacial surface between the layer 201 and air) cannot be directly found from the power spectrum. That is to say, in the example shown in FIG. 6, the film thicknesses and the refraction factors of the layers 201 to 203 were previously known. Therefore, it was possible to determine that the peak emerging at 4.8 μm indicates the optical film thickness of the layer 203. However, in the case where the film thicknesses and the refraction factors of the layers 201 to 203 are unknown, it cannot be identified that the peak emerging at 4.8 μm indicates the optical film thickness of the layer 203.

In the conventional apparatus and method for measuring film thickness, in the case of measuring a multilayer thin film having a plurality of layers with substantially equal optical film thicknesses, the peaks of the power spectrum overlap with each other. Therefore, the conventional apparatus and method for measuring film thickness has a problem that it is not possible to measure the optical film thickness of only one layer. FIG. 7A and FIG. 7B are graphs showing another example of power spectrums obtained by the conventional film thickness measuring apparatus 100. FIG. 7A and FIG. 7B show results of measuring the optical film thickness of the film 200 formed with the layer 201, the layer 202, and the layer 203. The refraction factor of the film 201 is 1.6 and the film thickness of the layer 201 is 3 μm. The refraction factor of the film 202 is 1.7 and the film thickness of the layer 202 is 12.7 μm. The refraction factor of the film 203 is 1.6 and the film thickness of the layer 203 is 3.2 μm.

Referring to FIG. 7A, reflected light from the interfacial surface related to the layer 201 and reflected light from the interfacial surface related to the layer 203 interfere with each other. This interference generates a peak P201 which is substantially an average of the peak indicating the optical film thickness of the layer 201 and the peak indicating the optical film thickness of the layer 203. Similarly, the interference generates a peak P203 which is substantially an average of: the peak indicating the sum of the optical film thickness of the layer 201 and the optical film thickness of the layer 202; and the peak indicating the sum of the optical film thickness of the layer 202 and the optical film thickness of the layer 203. Referring to FIG. 7B, reflected light from the interfacial surface related to the layer 201 and reflected light from the interfacial surface related to the layer 203 mutually cancel each other. As a result, peaks P301 and P303 with extremely small values are obtained. If a film thickness is measured using such peaks P201, P203, P301, and P303, there will be a problem that a significant measurement error may occur.

In recent years, for high function films and the like, a structure that is symmetric about the center (hereinafter, referred to as symmetric structure) is often used. For example, the following structure is often used. That is to say, a structure "ABA" with the center layer as "B" and with the layer "B" sandwiched by layers "A" of the same film thickness, or a structure "ABCBA" with the center layer as "C". When the film thickness of a multilayer thin film having such a symmetric structure is to be measured using the conventional apparatus and method for measuring film thickness, there is often a problem in the measurement due to the reason described with reference to FIG. 7A and FIG. 7B. Therefore, there is urgently needed a development of a technique for online-measuring the film thickness of each layer of a symmetrically structured multilayer thin film.

If a manufactured multilayer thin film is extracted and is offline-measured using a vertical scanning type white light interferometer, it is still possible to measure the film thickness of each layer of the multilayer thin film even with a symmetric structure. However, this measuring method has a problem that a measurement at one point requires a period of time ranging from several tens of seconds to several minutes. Moreover, since the measurement takes a long period of time, there is a problem that an error may occur in the measurement result due to vibrations of the multilayer thin film during the measurement, and the error becomes more significant for a thinner multilayer thin film.

SUMMARY OF THE INVENTION

The present invention takes into consideration the above circumstances. An object of the present invention is to provide an apparatus and method for measuring a film thickness that are capable of independently measuring the film thickness of each layer of even a multilayer thin film in which a plurality of layers with the same film thicknesses is present, at a high level of precision in a short period of time.

In order to solve the above problems, the film thickness measuring apparatus of the present invention comprises: a light source that emits white light to be irradiated onto a multilayer thin film; a spectroscope that disperses reflected light obtained as a result of irradiating the white light onto the multilayer thin film in order to obtain reflectance spectrums; and a computation section, said computation section including: a setting section that sets a plurality of wavelength ranges for the reflectance spectrums; a first conversion section that obtains wavenumber range reflectance spectrums by re-sequencing, among the reflectance spectrums, reflectance spectrums in the plurality of wavelength ranges set in said setting section at equal intervals, respectively; a second conversion section that converts the wavenumber range reflectance spectrums in the plurality of wavelength ranges obtained in said first conversion section into power spectrums, respectively; and a calculation section that obtains a film thickness of the multilayer thin film based on the power spectrums.

According to such a configuration, when white light from the light source is irradiated onto the multilayer thin film, the reflected light thereof is dispersed in the spectroscope, and reflectance spectrums are obtained. Among these reflectance spectrums, the reflectance spectrums in the plurality of wavelength ranges set in the setting section are respectively converted into wavenumber range reflectance spectrums. Subsequently, the respective wavenumber range reflectance spectrums are respectively converted into power spectrums. Then the film thickness of the multilayer thin film is found based on the power spectrums.

In the film thickness measuring apparatus of the present invention, said setting section may set a plurality of wavelength ranges with different transmittances for the multilayer thin film for the reflectance spectrums.

In the film thickness measuring apparatus of the present invention, said light source may be a pulse light source that emits pulsed white light, and said film thickness measuring apparatus may further includes a timing generating section that generates a timing signal for prescribing a light emission timing of said pulse light source and a timing for obtaining the reflected light in said spectroscope The film thickness measuring apparatus of the present invention may further comprise a velocity input section that receives an input of a flow velocity of the multilayer thin film, said timing generating section generating the timing signal based on the input of the flow velocity from said velocity input section, and on intervals of measurement points at which film thicknesses of the multilayer thin film are measured.

In the film thickness measuring apparatus of the present invention, said light source may include: a first light source that irradiates the white light onto one surface of the multilayer thin film; and a second light source that irradiates the white light onto the other surface of the multilayer thin film.

In the film thickness measuring apparatus of the present invention said spectroscope may include: a first spectroscope that disperses reflected light obtained as a result of irradiating the white light from said first light source onto one surface of the multilayer thin film in order to obtain a first reflectance spectrum; and a second spectroscope that disperses reflected light obtained as a result of irradiating the white light from said second light source onto the other surface of the multilayer thin film in order to obtain a second reflectance spectrum.

In the film thickness measuring apparatus of the present invention said computation section may perform processing in said first conversion section, said second conversion section, and said calculation section for the first reflectance spectrum and the second reflectance spectrum respectively obtained in said first spectroscope and said second spectroscope.

In the film thickness measuring apparatus of the present invention at least one wavelength range among the plurality of wavelength ranges set in said setting section may be a wavelength range with a transmittance of no more than 50%.

The film thickness measuring method of the present invention comprises: a setting step of setting a plurality of wavelength ranges with different transmittances for a multilayer thin film; a first conversion step of obtaining reflectance spectrums by dispersing reflected light obtained as a result of irradiating white light onto the multilayer thin film, and obtaining wavenumber range reflectance spectrums by re-sequencing, among the reflectance spectrums, reflectance spectrums in the plurality of wavelength ranges set in the setting step at equal intervals, respectively; a second conversion step of converting the wavenumber range reflectance spectrums in the plurality of wavelength ranges obtained in the first conversion step into power spectrums, respectively; and a thickness calculation step of obtaining a film thickness of the multilayer thin film based on the power spectrums.

According to the present invention, a plurality of power spectrums are found from the reflectance spectrums in the plurality of wavelength ranges (for example, high transmittance wavelength range and low transmittance wavelength range with respect to the multilayer thin film) set in the setting section, among the reflectance spectrums of the reflected light obtained as a result of irradiating the white light onto the multilayer thin film. Furthermore, the film thickness of the multilayer thin film is found based on this plurality of power spectrums. Therefore, the film thickness of a portion close to the top surface of the multilayer thin film and the film thickness of the entire multilayer thin film can be found. As a result, there is achieved an effect that even if a plurality of layers with similar film thicknesses is present in the multilayer thin film, the film thickness of each layer can be independently measured at a high level of precision in a short period of time.

DETAILED DESCRIPTION OF THE INVENTION

Hereinafter, an apparatus and method for measuring film thickness according to embodiments of the present invention are described in detail, with reference to the drawings.

First Embodiment

Figure 1:
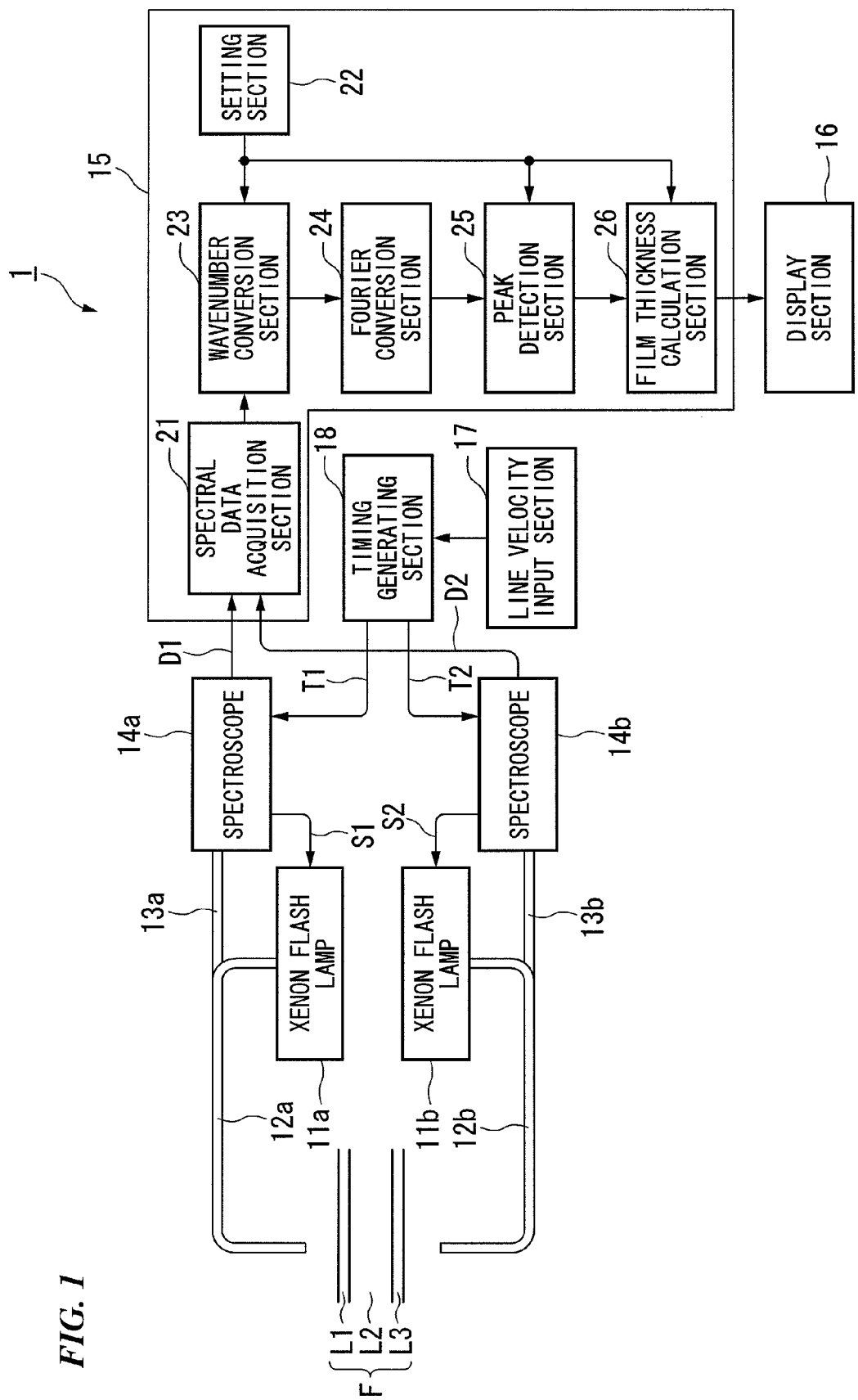
FIG. 1 is a block diagram showing a configuration of principal portions of a film thickness measuring apparatus according to a first embodiment of the present invention.

FIG. 1 is a block diagram showing a configuration of principal portions of a film thickness measuring apparatus according to a first embodiment of the present invention. As shown in FIG. 1, a film thickness measuring apparatus 1 of the present embodiment includes a xenon flash lamp 11a (first light source), a xenon flash lamp 11b (second light source), irradiation fibers 12a and 12b, light receiving fibers 13a and 13b, a spectroscope 14a (first spectroscope), a spectroscope 14b (second spectroscope), a computation section 15, a display section 16, a line velocity input section 17, and a timing generating section 18. The film thickness measuring apparatus 1 measures the film thickness of a film F formed with a plurality of layers L1 to L3. The film F is a multilayer thin film such as a flexible substrate, a multilayer composite film sheet, and other kinds of multilayer thin film.

The xenon flash lamps 11a and 11b emit white light of a wide wavelength range, several hundred nanometers to one thousand and several hundred nanometers, to be irradiated onto the film F. The xenon flash lamps 11a and 11b are pulse light sources that emit white light in synchronization with synchronization signals S1 and S2 outputted from the spectroscopes 14a and 14b. The irradiation fibers 12a and 12b are light guiding members that guide the pulsed white light emitted from the xenon flash lamps 11a and 11b to the film F so as to irradiate the light onto the film F. Specifically, the irradiation fiber 12a guides the white light emitted from the xenon flash lamp 11a so that the light is irradiated from a layer L1 side onto the film F. The irradiation fiber 12b guides the white light emitted from the xenon flash lamp 11b so that the light is irradiated from a layer L3 side onto the film F.

The light receiving fibers 13a and 13b are light guiding members that guide the reflected light from the film F respectively to the spectroscopes 14a and 14b. Specifically, the incident end of the light receiving fiber 13a is arranged on the layer L1 side of the film F. The light receiving fiber 13a guides the reflected light on the layer L1 side to the spectroscope 14a. On the other hand, the incident end of the light receiving fiber 13b is arranged on the layer L3 side of the film F. The light receiving fiber 13b guides the reflected light on the layer L3 side to the spectroscope 14b. The incident ends of the light receiving fibers 13a and 13b are positioned so that the white light transmitted through the film F is not incident from the incident end.

The spectroscopes 14a and 14b respectively disperse the reflected light from the film F guided by the light receiving fibers 13a and 13b. Furthermore, the spectroscopes 14a and 14b perform a photoelectric conversion on the dispersed light and output it as spectral data D1 and D2 that indicate reflectance spectrums. Specifically, the spectroscopes 14a and 14b are provided with a dispersive device such as prism and diffraction grating for dispersing the reflected light, and the spectroscopes 14a and 14b are further provided with a photoelectric conversion device such as a CCD (charge coupled device) for photoelectrically converting the dispersed light.

The computation section 15 includes a spectral data acquisition section 21, a setting section 22, a wavenumber conversion section 23 (first conversion section), a Fourier conversion section 24 (second conversion section), a peak detection section 25 (calculation section), and a film thickness calculation section 26 (calculation section). The computation section 15 performs a predetermined computation for the spectral data D1 and D2 outputted from the spectroscopes 14a and 14b to obtain the film thickness of the film F. The spectral data acquisition section 21 acquires the spectral data D1 outputted from the spectroscope 14a and the spectral data D2 outputted from the spectroscope 14b. That is to say, the spectral data acquisition section 21 acquires reflectance spectrums obtained from the respective surfaces of the film F.

The setting section 22 sets a plurality of wavelength ranges with different transmission factors for the film F.

For example, the film F has a transmission characteristic where its transmission factor declines as the wavelength becomes shorter, and the transmission factor of the film F is no more than 50% (0 to 50%) for wavelengths no more than 500 nm and is no less than 50% (50 to 100%) for wavelengths no less than 500 nm. In this case, the wavelength range for wavelengths no more than 500 nm (for example, 300 to 500 nm) is set as a first wavelength range, and the wavelength for wavelengths no less than 500 nm (for example, 500 to 1000 nm) is set as a second wavelength range.

Here, in order to simplify the following description, there is provided, as an example, a case where a wavelength range of wavelengths no more than 500 nm in which the transmission factor of the film F is no more than 50% and a wavelength range of wavelengths no less than 500 nm in which the transmission factor of the film F is no less than 50% are set in the setting section 22. A transmission factor that determines the boundary between the wavelength ranges may be arbitrarily set. The transmission factor does not always have to be no less than or no more than 50% in all of the set wavelength ranges. For example, in the case where a wavelength range with a transmission factor no more than 50% (0 to 50%) is set, even if the transmission factor exceeds 50% for a certain wavelength within the wavelength range, it is acceptable that an average transmission factor within the entire wavelength range is no more than 50% (0 to 50%). The wavelength range that is set in the setting section 22 can be freely set by a user according to the transmission characteristic of the film F.

The setting section 22 sets a range (hereinafter, referred to as peak detection range) for detecting a peak of a power spectrum (described in detail later) used for measuring the film thickness of the film F. For example, in the case where the optical film thickness of the entire film F is no more than 40 μm, a range of no more than 40 μm is set as a peak detection range. Furthermore, the setting section 22 sets a refraction factor for each wavelength of the respective layers L1 to L3 that form the film F. Thereby, it is possible to convert an optical film thickness into an actual film thickness (physical film thickness). The above peak detection range and the refraction factor can be freely set by a user according to the structure of the film F.

The wavenumber conversion section 23 converts reflectance spectrums within a certain wavelength range into wavenumber range reflectance spectrums re-sequenced at equal wavenumber intervals. Specifically, the wavenumber conversion section 23 selects the spectral data in the wavelength range set in the setting section 22 from each of the spectral data D1 and D2 that indicate reflectance spectrums obtained by the spectral data acquisition section 21. Next, the wavenumber conversion section 23 performs a predetermined processing on the selected spectral data D1 and D2. Thereby, the wavenumber conversion section 23 converts the reflectance spectrums within the wavelength range into wavenumber range reflectance spectrums re-sequenced at equal wavenumber intervals. The Fourier conversion section 24 performs Fourier conversion on the data that indicate the wavenumber range reflectance spectrum converted in the wavenumber conversion section 23 so as to convert it into a power spectrum in each of the wavelength ranges set in the setting section 22.

The peak detection section 25 detects a peak of the power spectrum within the peak detection range set in the setting section 22. Based on the position of the peak of the power spectrum, the optical film thicknesses of the respective layers L1 to L3 forming the film F and the optical film thickness of the film F are found. The film thickness calculation section 26 uses the refraction factor set in the setting section 22 to find the actual film thickness of the film F.

The display section 16 is provided with a display device such as a CRT (cathode ray tube) or a liquid crystal display device. The display section 16 displays the film thickness of the film F calculated by the film thickness calculation section 26. Although not shown in FIG. 1, the spectral data D1 and D2 obtained in the spectral data acquisition section 21 or the power spectrum converted in the Fourier conversion section 24 may be displayed on the display section 16.

The line velocity input section 17 receives an input of flow velocity of the film F, which is the measurement object. The film F is not stationary with respect to the irradiation fibers 12a, 12b and the light receiving fibers 13a, 13b. The film F flows between: the irradiation fiber 12a and the light receiving fiber 13a; and the irradiation fiber 12b and the light receiving fiber 13b, at constant velocity. This flow velocity of the film F is inputted from the line velocity input section 17. In the case where the flow velocity of the film F changes, it is preferable that the actual flow velocity of the film F is measured, and then this measurement result is inputted to the line velocity input section 17.

In order to measure, at constant intervals, the film F flowing at constant velocity, the timing generating section 18 generates timing signals T1 and T2 that prescribe timings for the spectroscopes 14a and 14b to obtain reflected light, based on the flow velocity of the film F that has been inputted from the line velocity input section 17 and on the pre-set interval for measuring the film F. Based on these timing signals T1 and T2, synchronization signals S1 and S2 that prescribe light emission timings for the xenon flash lamps 11a and 11b are respectively generated.

Next, a film thickness measuring method according to the first embodiment of the present invention is described. The user pre-sets a plurality of wavelength ranges, a refraction factor for each wavelength of the layers L1 to L3, and a peak detection range, in the setting section 22 according to the transmission characteristic and structure of the film F, which is the measurement object. The user pre-inputs the flow velocity of the film F into the line velocity input section 17. In the timing generating section 18, there has already been set measurement intervals of the film F.

Once the film thickness measurement for the film F has commenced, timing signals T1 and T2 are generated in the timing generating section 18 based on the flow velocity inputted from the line velocity input section 17 and the pre-set measurement intervals for the film F. These timing signals T1 and T2 are respectively outputted to the spectroscopes 14a and 14b. When the timing signals T1 and T2 have been inputted to the spectroscopes 14 and 14b, synchronization signals S1 and S2 are generated in the spectroscopes 14a and 14b based on these timing signals T1 and T2 so as to be respectively outputted to the xenon flash lamps 11a and 11b. Thereby, light emission from the xenon flash lamps 11a and 11b is commenced.

Figure 2:
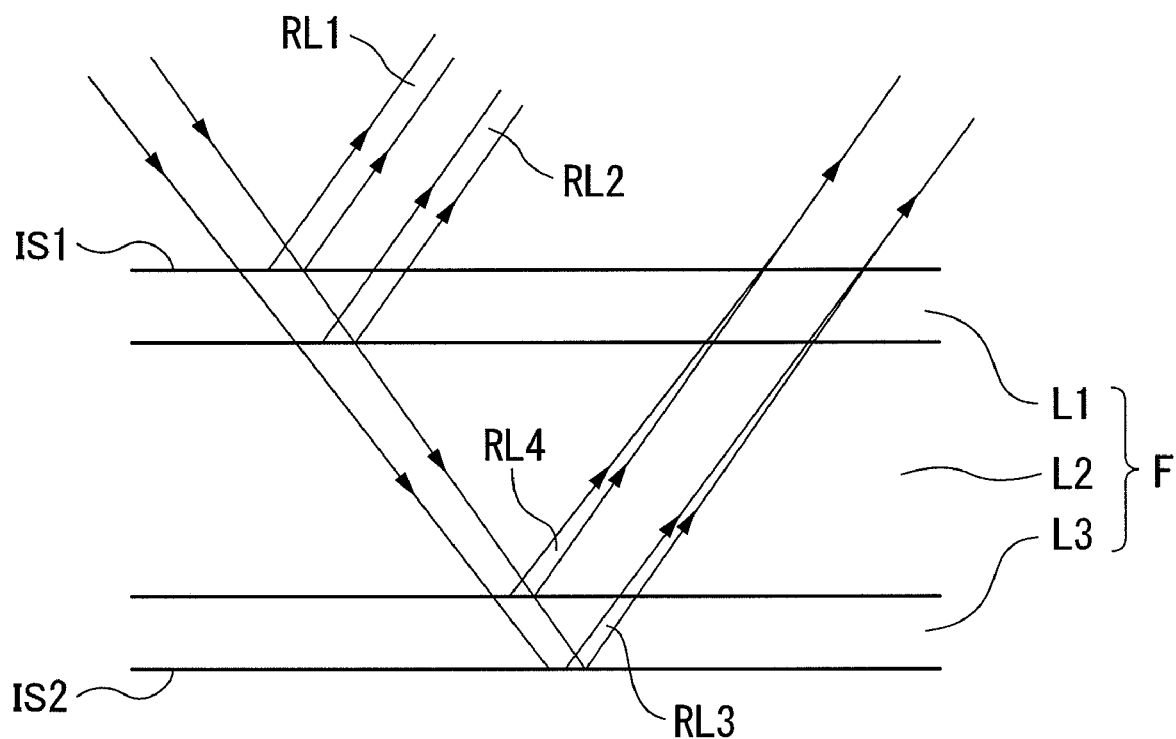
FIG. 2 is a diagram schematically showing a state where light of a low transmittance wavelength range among white light irradiated onto a film by the film thickness measuring apparatus shown in FIG. 1, is being reflected and absorbed.

The pulsed white light emitted from the xenon flash lamp 11a is irradiated from the layer L1 side, via the irradiation fiber 12a, onto the film F. Similarly, the pulsed white light emitted from the xenon flash lamp 11b is irradiated from the layer L3 side, via the irradiation fiber 12b, onto the film F. FIG. 2 is a diagram schematically showing a state where light of a low transmittance wavelength range among the white light irradiated by the film thickness measuring apparatus 1 onto the film F is being reflected and absorbed. In order to facilitate understanding, FIG. 2 shows a state where white light is diagonally incident on the film F. However, in reality white light is substantially perpendicularly incident on the film F.

The light of a low transmittance wavelength range among the white light irradiated from the layer L1 side of the film F is absorbed by the film F. Therefore, as shown in FIG. 2, reflected light RL1 from one top most surface IS1 of the film F or reflected light RL2 from an interfacial surface that is close to the top most surface IS1 (interfacial surface between the layer L1 and the layer L2) returns to the incident end of the light receiving fiber 13a. Since reflected light RL3 from the other top most surface IS2 or reflected light RL4 from an interfacial surface that is close to the top most surface IS2 is absorbed by the film F, the amount of the light returning to the incident end of the light receiving fiber 13a is extremely small.

On the other hand, in the case of the light of a high transmittance wavelength range among the white light irradiated from the layer L1 side of the film F, this returns to the incident end of the light receiving fiber 13a, regardless of whether it is reflected light from the top most surface IS1 or from the interfacial surface close to the top most surface IS1, or reflected light from the top most surface IS2 or from the interfacial surface close to the top most surface IS2.

Therefore, if light of a low transmittance wavelength range is used, the structure of a portion that is close to the top most surface IS1 (film thickness) of the film F, can be found. On the other hand, if light of a high transmittance wavelength range is used, then the entire structure (film thickness) of the film F can be found.

Similarly, the light of a low transmittance wavelength range among the white light irradiated from the layer L3 side of the film F is absorbed easily by the film F, and absorption of the light of a high transmittance wavelength range on the film F is small. Therefore, if light of a low transmittance wavelength range is used, the structure of a portion that is close to the top most surface IS2 (film thickness) of the film F, can be found. If light of a high transmittance wavelength range is used, then the entire structure (film thickness) of the film F can be found.

The reflected light that has been incident on the light receiving fibers 13a and 13b is respectively guided to the spectroscopes 14a and 14b. The guided reflected light is dispersed in the spectroscopes 14a and 14b, and furthermore it is photoelectrically converted. Thereby, the spectral data D1 and D2 that indicate reflectance spectrums are acquired from the spectroscopes 14a and 14b. The spectral data D1 and D2 outputted from the spectroscopes 14a and 14b are acquired by the spectral data acquisition section 21 of the computation section 15. The spectral data acquisition section 21 outputs the acquired spectral data D1 and D2 to the wavenumber conversion section 23.

The wavenumber conversion section 23 selects the spectral data in the wavelength range set in the setting section 22 from each of the spectral data D1 and D2 that indicate the reflectance spectrums from the spectral data acquisition section 21. That is to say, from each of the spectral data D1 and D2, spectral data that indicates the reflectance spectrum in the wavelength range with a low transmittance with respect to the film F, and spectral data that indicates the reflectance spectrum in the wavelength range with a high transmittance with respect to the film F, are selected.

The wavenumber conversion section 23 converts the reflectance spectrums in the wavelength range into wavenumber range reflectance spectrums that are the reflectance spectrums in the wavelength range re-sequenced at equal wavenumber intervals by performing a predetermined processing on the selected spectral data. The wavenumber range reflectance spectrums outputted from the wavenumber conversion section 23 are inputted to the Fourier conversion section 24. The Fourier conversion section 24 performs Fourier conversion on the inputted wavenumber range reflectance spectrums. Thereby, a power spectrum in each of the wavelength ranges set in the setting section 22 among the reflected light obtained from the layer L1 side can be found. Furthermore, a power spectrum in each of the wavelength ranges set in the setting section 22 among the reflected light obtained from the layer L3 side can be found.

Figure 3:
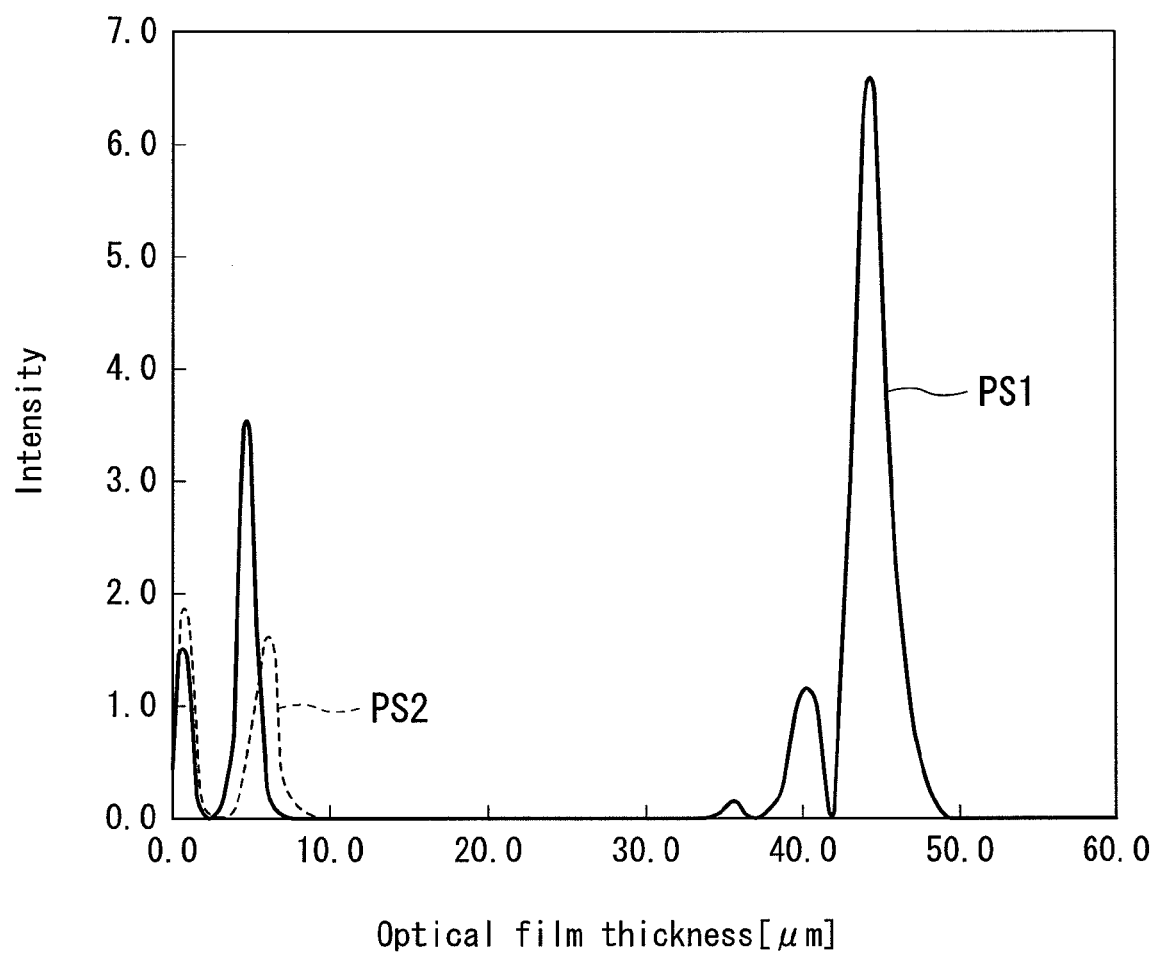
FIG. 3 is a graph showing an example of power spectrums obtained from the reflected light on the side of a layer L1 generated from the white light irradiated by the film thickness measuring apparatus shown in FIG. 1.

FIG. 3 is a graph showing an example of power spectrums obtained from reflected light on the layer L1 side generated from the white light irradiated by the film thickness measuring apparatus 1. In FIG. 3, the curved solid line PS1 shows a power spectrum in a wavelength range with high transmittance with respect to the film F. The curved broken line PS2 shows a power spectrum in a wavelength range with low transmittance with respect to the film F. In the graph shown in FIG. 3, the horizontal axis represents the optical film thickness, and the vertical axis represents the intensity (arbitrary units).

Referring to FIG. 3, a peak occurs in the power spectrum PS1, which shows the power spectrum in the high transmittance wavelength range, even in the case where the optical film thickness is approximately 45 μm. On the other hand, no peak occurs in the power spectrum PS2, which shows the power spectrum in the low transmittance wavelength range, where the optical film thickness is no less than 10 μm. This is due to the reason that has been described with reference to FIG. 2. That is to say, in the high transmittance wavelength range, reflected light from the top most surface IS2 is obtained. On the other hand, in the low transmittance wavelength range, reflected light from the top most surface IS2 and reflected light from the interfacial surface between the layer L2 and L3 are hardly obtained due to the absorption within the film F.

Referring to FIG. 3, it can be seen that in the range where the optical film thickness is no more than 10 μm, the power spectrum PS1 shown with the solid line, which shows the power spectrum in the high transmittance wavelength range and the power spectrum PS2 shown with the broken line, which shows the power spectrum in the low transmittance wavelength range are clearly separated. The power spectrum PS2, which shows the power spectrum in the low transmittance wavelength range shows the structure (film thickness) of the portion close to the top most surface IS1. Therefore, even if the film thicknesses of the layer L1 and the layer L2 of the film F are substantially equal to each other, it is possible to find only the optical film thickness of the layer L1 that is close to the top most surface IS1 at a high level of precision. From the power spectrum PS1, which shows the power spectrum in the high transmittance wavelength range, the optical film thickness of the entire film F can be found at a high level of precision.

As with the case shown in FIG. 3, also from the reflected light on the layer L3 side, the power spectrum in the high transmittance wavelength range and the power spectrum in the low transmittance wavelength range can be obtained. This power spectrum in the low transmittance wavelength range shows the structure (film thickness) of the portion close to the top most surface IS2. Therefore, even if the film thicknesses of the layer L1 and the layer L3 of the film F are substantially equal to each other, it is possible to find only the optical film thickness of the layer L3 that is close to the top most surface IS2 at a high level of precision.

The power spectrum obtained in the Fourier conversion section 24 is outputted to the peak detection section 25. The peak detection section 25 detects a peak of the power spectrum within the peak detection range set in the setting section 22 from the inputted power spectrum. As a result, the optical film thicknesses of the layers L1 and L3 of the film F and the optical film thickness of the entire film F can be found. When the peak of the power spectrum has been detected, the film thickness calculation section 26 finds the actual film thickness of the film F, using the obtained optical film thickness and the refraction factor set in the setting section 22.

Specifically, the film thickness is found as described below. The optical film thicknesses of the layers L1 and L3 of the film F and that of the entire film F that are found in the peak detection section 25 are respectively taken as $l_1$, $l_2$, and $l_3$. The refraction factors in the low transmittance wavelength range of the layers L1 to L3 are respectively taken as $n_{11}$ to $n_{13}$. The refraction factors in the high transmittance wavelength range are respectively taken as $n_{21}$ to $n_{23}$. The film thickness calculation section 26 uses the following expression (1) to find the film thicknesses $d_1$ to $d_3$ of the layers L1 to L3 of the film F.

$$d_1 = l_1/n_{11}$$

$$d_2 = (l_3 - (d_1 \cdot n_{21} + d_3 \cdot n_{23}))/n_{22}$$

$$d_3 = l_2/n_{13} \quad (1)$$

When the film thicknesses of the respective layers L1 to L3 of the film F have been calculated, the calculation results are displayed on the display section 16. In addition to the calculation results of the film thicknesses of the respective layers L1 to L3, the spectral data D1 and D2 acquired in the spectral data acquisition section 21 or the power spectrum converted in the Fourier conversion section 24 may be displayed on the display section 16. By making reference to the display contents of the display section 16, the user can confirm whether or not the film F has been manufactured as designed. Based on the film thicknesses measured in the above process, a manufacturing apparatus that manufactures the film F may be automatically controlled so that the film thicknesses of the respective layers L1 to L3 match the design values.

Second Embodiment

Figure 4:
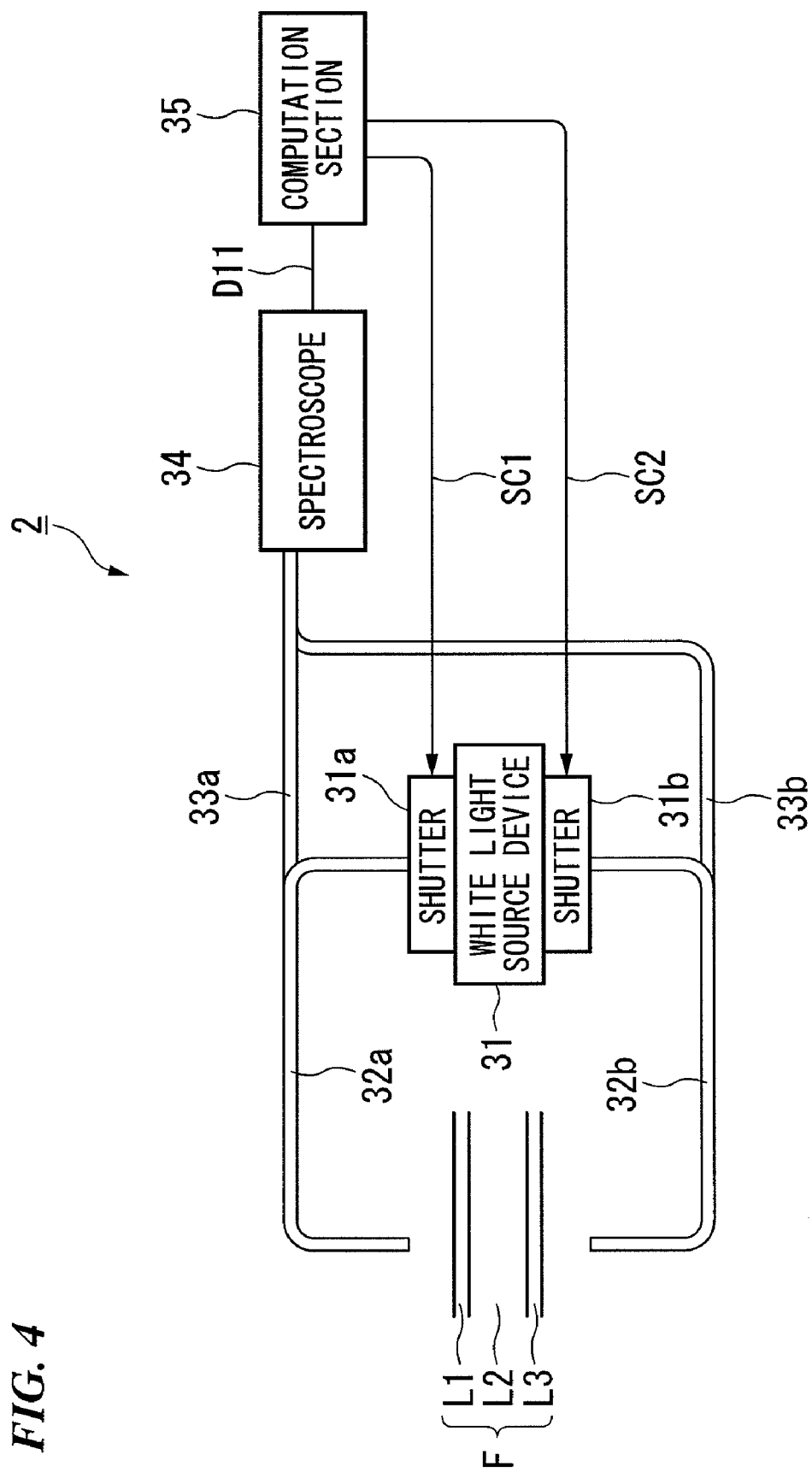
FIG. 4 is a block diagram showing a configuration of principal portions of a film thickness measuring apparatus according to a second embodiment of the present invention.
Figure 5:
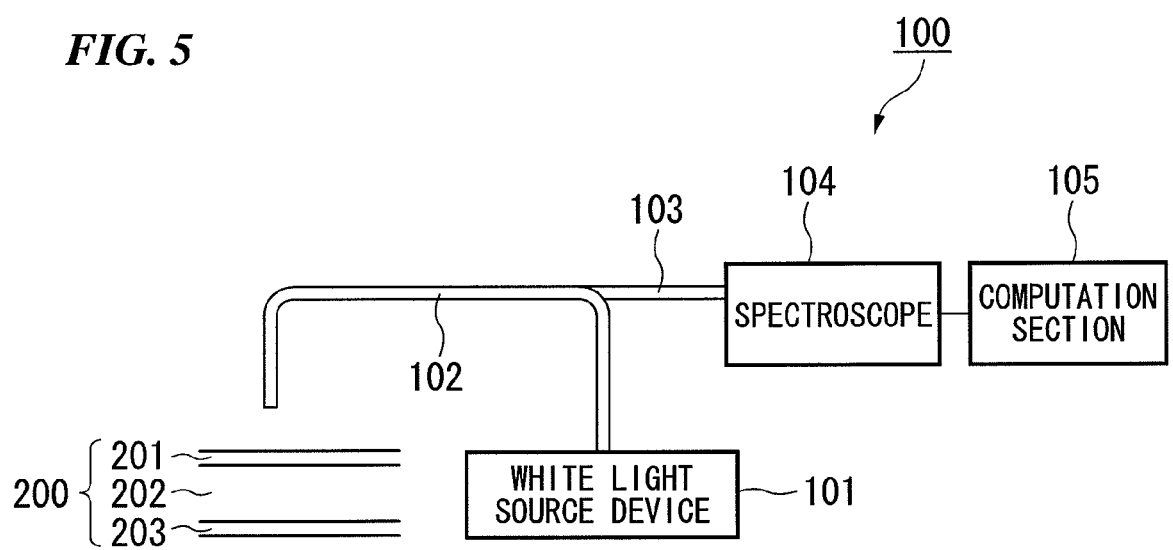
FIG. 5 is a diagram showing a schematic configuration of a conventional film thickness measuring apparatus.
Figure 6:
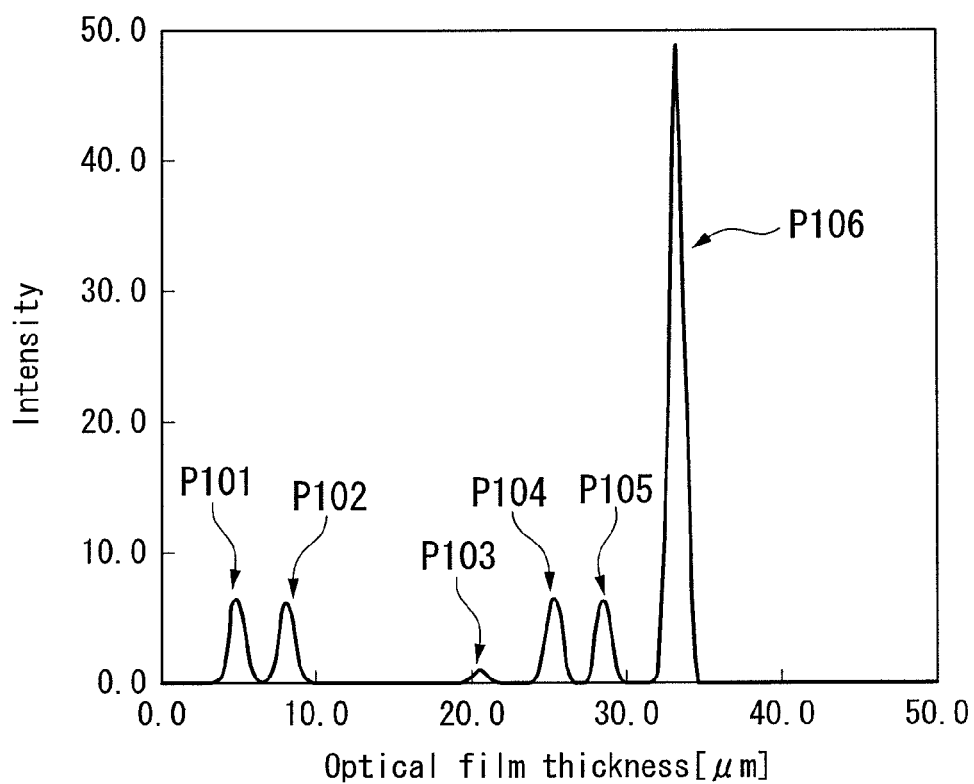
FIG. 6 is a graph showing an example of a power spectrum obtained by the conventional film thickness measuring apparatus.
Figure 7A:
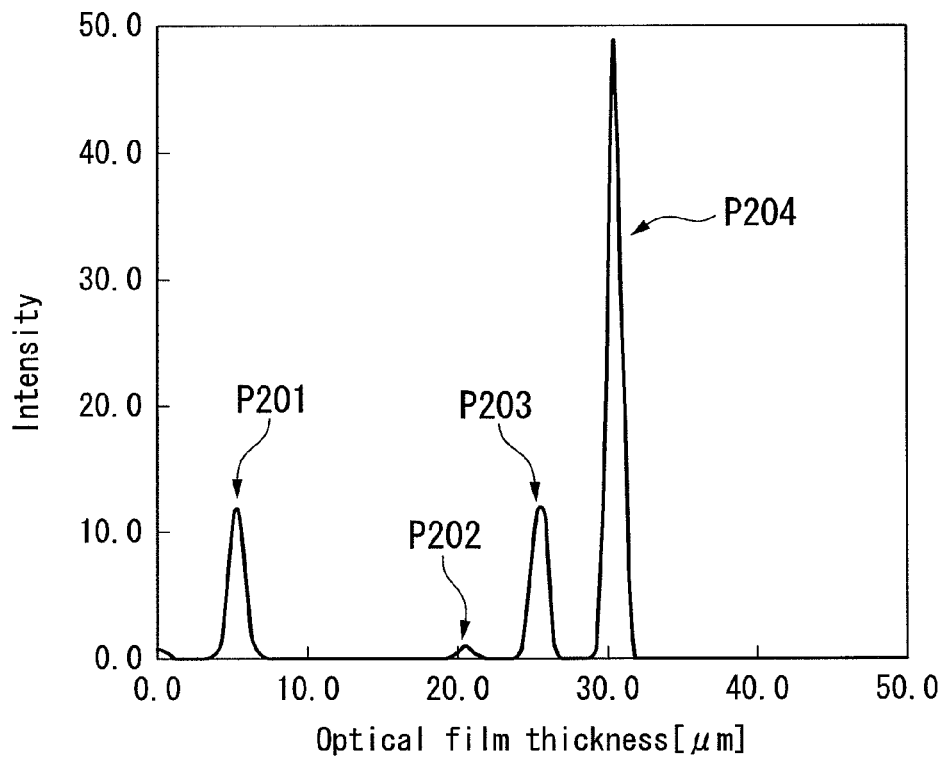
FIG. 7A is a graph showing another example of a power spectrum obtained by the conventional film thickness measuring apparatus.
Figure 7B:
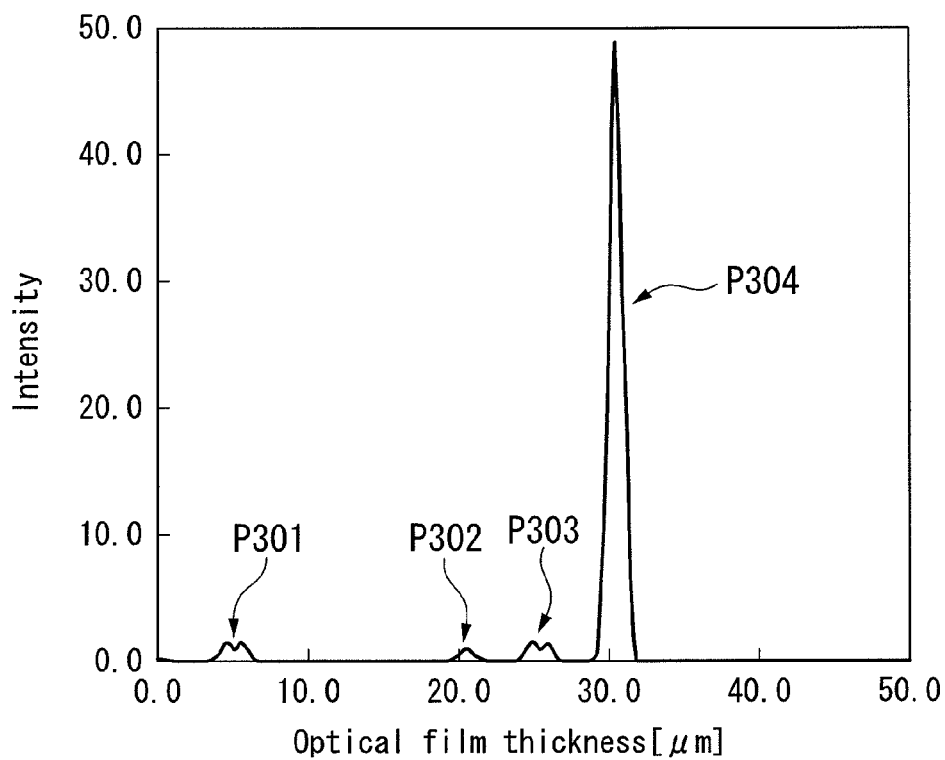
FIG. 7B is a graph showing still another example of a power spectrum obtained by the conventional film thickness measuring apparatus.

FIG. 4 is a block diagram showing a configuration of principal portions of a film thickness measuring apparatus according to a second embodiment of the present invention. As shown in FIG. 4, a film thickness measuring apparatus 2 of the present embodiment includes a white light source device 31, shutters 31a and 31b, irradiation fibers 32a and 32b, light receiving fibers 33a and 33b, a spectroscope 34, and a computation section 35. The film thickness measuring apparatus 2 measures the film thickness of a film F formed with a plurality of layers L1 to L3. As with the case of the first embodiment, the film F is a multilayer thin film such as a flexible substrate, a multilayer composite film sheet, and other kinds of multilayer thin film.

The white light source device 31 is a light source that emits white light of a wide wavelength range, several hundred nanometers to one thousand and several hundred nanometers, to be irradiated onto the film F. The white light source device 31 differs from the xenon flash lamps 11a and 11b shown in FIG. 1. The white light source device 31 continuously emits white light. The shutters 31a and 31b control the opening and closing of an optical path between the white light source device 31 and the irradiation fiber 32a and of an optical path between the white light source device 31 and the irradiation fiber 32b, based on shutter control signals SC1 and SC2 outputted from the computation section 35.

The irradiation fibers 32a and 32b are light guiding members as with the irradiation fibers 12a and 12b shown in FIG. 1. The fibers 32a and 32b guide the white light that has been emitted from the white light source device 31 and has passed through the shutters 31a and 31b, so as to irradiate the white light onto the film F. Specifically, the irradiation fiber 32a guides the white light that has passed through the shutter 31a so that the light is irradiated from the layer L1 side onto the film F. The irradiation fiber 32b guides the white light that has passed through the shutter 31b so that the light is irradiated from the layer L3 side onto the film F.

The light receiving fibers 33a and 33b are light guiding members that guide reflected light on the layer L1 side of the film F and reflected light on the layer L3 side respectively to the spectroscope 34. The incident end of the light receiving fiber 33a is arranged on the layer L1 side of the film F. The incident end of the light receiving fiber 33a is arranged on the layer L3 side of the film F. In the present embodiment, these incident ends may be arranged on an axis perpendicular to the film F.

The spectroscope 34 is provided with a dispersive device such as a prism and a diffraction grating, and a photoelectric conversion device such as a CCD. The spectroscope 34 respectively disperses the reflected lights from the film F that have been guided by the light receiving fibers 33a and 33b, photoelectrically converts the dispersed light, and outputs a spectral data D11 indicating the reflectance spectrum. The computation section 35 includes the spectral data acquisition section 21, the setting section 22, the wavenumber conversion section 23, the Fourier conversion section 24, the peak detection section 25, and the film thickness calculation section 26, shown in FIG. 1. The computation section 35 performs a predetermined computation for the spectral data D11 outputted from the spectroscope 34 to measure the film thickness of the film F. In addition, the computation section 35 generates shutter control signals SC1 and SC2 for controlling the opening and closing of the shutters 31a and 31b.

Next, a film thickness measuring method according to the second embodiment of the present invention is described. As with the case of the first embodiment, the user pre-sets a plurality of wavelength ranges, a refraction factor for each wavelength of the layers L1 to L3, and a peak detection range, in the setting section 22 provided in the computation section 35 (not shown in FIG. 4) according to the transmission characteristic and structure of the film F, which is the measurement object.

When a film thickness measurement for the film F has commenced, the computation section 35 outputs a shutter control signal SC1, and the shutter 31a is brought to the open state. As a result, the white light emitted from the white light source device 31 is irradiated from the layer L1 side, via the shutter 31a and the irradiation fiber 32a, onto the film F. The reflected light of the white light irradiated onto the layer L1 side of the film F is incident on the incident end of the light receiving fiber 33a. The reflected light that has been incident on the light receiving fiber 33a is guided to the spectroscope 34 so as to be dispersed, and then it is photoelectrically converted.

Thereby, the spectroscope 34 obtains spectral data D11 indicating the reflectance spectrum of the reflected light obtained from the layer L1 side of the film F. The spectroscope 34 outputs this spectral data D11 to the computation section 35. When this spectral data D11 has been inputted to the computation section 35, a process that is similar to the process performed in the first embodiment, is performed to find the power spectrum, thereby calculating the optical film thickness of the layer L1 of the film F and that of the entire film F.

When the above process is complete, the output of the shutter control signal SC1 is stopped and the shutter 31a is brought to the close state, and the computation section 35 outputs a shutter control signal SC2 to bring the shutter 31b to the open state. As a result, the white light emitted from the white light source device 31 is irradiated from the layer L3 side, via the shutter 31b and the irradiation fiber 32b, onto the film F. The reflected light from the layer L3 side of the film F is incident on the incident end of the light receiving fiber 33b.

The light receiving fiber 33b guides the incoming reflected light to the spectroscope 34, and the spectroscope 34 disperses the guided reflected light and photoelectrically converts it.

Thereby, the spectral data D11 indicating the reflectance spectrum of the reflected light obtained from the layer L3 side of the film F is obtained from the spectroscope 34. The spectroscope 34 outputs this spectral data D11 to the computation section 35. When this spectral data D11 has been inputted to the computation section 35, a process that is similar to the process performed in the first embodiment, is performed to find the power spectrum. From this power spectrum, the optical film thickness of the layer L3 of the film F and that of the entire film F are calculated.

By performing the above process, the optical film thickness of the layer L1 of the film F, the optical film thickness of the layer L3, and the optical film thickness of the entire film F are calculated. Based on these optical thickness values, the computation section 35 uses the expression (1) to respectively calculate the film thicknesses of the layers L1 to L3 that form the film F. Hereafter, a process similar to that described above is repeated to measure the film thickness of another part of the film F or to measure the film thickness of another film F.

The film thickness measuring apparatus 2 of the present embodiment can be used not only in the case of measuring the film thickness of a flowing film F, but also in the case of measuring the film thickness of a stationary film F. In the case where the film thickness of the stationary film F is measured, the configuration may omit the shutter 31b, the irradiation fiber 32b, and the light receiving fiber 33b. In the case of such a configuration, white light is irradiated from the layer L1 side onto the film F to perform measurement. As a result, the structure (film thickness) of the layer L1 side can be measured at a high level of precision. Furthermore, having irradiated the white light from the layer L1 side onto the film F and performing measurement, the film F is turned over. In this state where the film F has been turned over, white light is irradiated from the layer L3 side onto the film F to perform measurement. As a result, the structures (film thicknesses) of both the layer L1 side and the layer L3 side can be measured at a high level of precision.

As described above, in the present embodiment, the process is performed as follows. That is to say, reflectance spectrums of the reflected light obtained by irradiating white light onto the film F are found. Among these reflectance spectrums, the reflectance spectrums in the plurality of pre-set wavelength ranges (for example, a high transmittance wavelength range and a low transmittance wavelength range with respect to the film F) are respectively converted into wavenumber range reflectance spectrums by re-sequencing them at equal wavenumber intervals. These converted wavenumber range reflectance spectrums are respectively converted into a power spectrum. From the peaks in this power spectrum, the film thicknesses of the layers L1 to L3 that form the film F are calculated. Accordingly, the structure (film thickness) of a portion close to the top surface of the film F and the structure (film thickness) of the entire film F can be found. As a result, even if a plurality of layers with similar film thicknesses is present in the film F, the film thickness of each layer can be independently measured at a high level of precision in a short period of time.

The apparatus and method for measuring film thickness according to the embodiments of the present invention have been described. However, the present invention is not limited to the above embodiments, and modifications can be freely made without departing from the scope of the invention. For example, in the above embodiments, the case of measuring the film thickness of the film F formed with three of the layers L1 to L3 is taken as an example. However, the present invention can be applied to the case of measuring the film thickness of a film formed from more than three layers. In the case where the measurement points do not significantly alter the film thickness, or where the required measurement precision is not high, either one or both of the line velocity input section 17 and the timing generating section 18 may be omitted.

Moreover, the case of setting a plurality of wavelength ranges with different transmittances for the multilayer thin film is illustrated for simultaneously measuring both film thicknesses of each layer and the film thickness of the entire film. However, a plurality of wavelength ranges may be set in the range where transmittances are not different. It is advantageous when measuring a plurality of layers in which each of the layers have very different thicknesses each other.

What is claimed is:

1. A film thickness measuring apparatus comprising:
   a light source that emits white light to be irradiated onto a multilayer thin film;
   a spectroscope that disperses reflected light obtained as a result of irradiating the white light onto the multilayer thin film in order to obtain reflectance spectrums; and
   a computation section, said computation section including:
   a setting section that sets a plurality of wavelength ranges for the reflectance spectrums;

a first conversion section that obtains wavenumber range reflectance spectrums by re-sequencing, among the reflectance spectrums, reflectance spectrums in the plurality of wavelength ranges set in said setting section at equal intervals, respectively;

a second conversion section that converts the wavenumber range reflectance spectrums in the plurality of wavelength ranges obtained in said first conversion section into power spectrums, respectively; and a calculation section that obtains a film thickness of the multilayer thin film based on the power spectrums.

2. A film thickness measuring apparatus according to claim 1, wherein said setting section sets a plurality of wavelength ranges with different transmittances for the multilayer thin film for the reflectance spectrums.

3. A film thickness measuring apparatus according to claim 1, wherein said light source is a pulse light source that emits pulsed white light, and said film thickness measuring apparatus further includes a timing generating section that generates a timing signal for prescribing a light emission timing of said pulse light source and a timing for obtaining the reflected light in said spectroscope.

4. A film thickness measuring apparatus according to claim 3, further comprising a velocity input section that receives an input of a flow velocity of the multilayer thin film, said timing generating section generating the timing signal based on the input of the flow velocity from said velocity input section, and on intervals of measurement points at which film thicknesses of the multilayer thin film are measured.

5. A film thickness measuring apparatus according to claim 1, wherein said light source includes:

a first light source that irradiates the white light onto one surface of the multilayer thin film; and a second light source that irradiates the white light onto the other surface of the multilayer thin film.

6. A film thickness measuring apparatus according to claim 1, wherein said spectroscope includes:

a first spectroscope that disperses reflected light obtained as a result of irradiating the white light from said first light source onto one surface of the multilayer thin film in order to obtain a first reflectance spectrum; and a second spectroscope that disperses reflected light obtained as a result of irradiating the white light from said second light source onto the other surface of the multilayer thin film in order to obtain a second reflectance spectrum.

7. A film thickness measuring apparatus according to claim 6, wherein said computation section performs processing in said first conversion section, said second conversion section, and said calculation section for the first reflectance spectrum and the second reflectance spectrum respectively obtained in said first spectroscope and said second spectroscope.

8. A film thickness measuring apparatus according to claim 2, wherein at least one wavelength range among the plurality of wavelength ranges set in said setting section is a wavelength range with a transmittance of no more than 50%.

9. A film thickness measuring method comprising:

a setting step of setting a plurality of wavelength ranges for reflectance spectrums;

a first conversion step of obtaining reflectance spectrums by dispersing reflected light obtained as a result of irradiating white light onto the multilayer thin film, and obtaining wavenumber range reflectance spectrums by re-sequencing, among the reflectance spectrums, reflectance spectrums in the plurality of wavelength ranges set in the setting step at equal intervals, respectively;

a second conversion step of converting the wavenumber range reflectance spectrums in the plurality of wavelength ranges obtained in the first conversion step into power spectrums, respectively; and a thickness calculation step of obtaining a film thickness of the multilayer thin film based on the power spectrums.

* * * * *